(12) United States Patent
Sagmeister et al.

(10) Patent No.: US 11,384,800 B2
(45) Date of Patent: Jul. 12, 2022

(54) JAMMING ROLLER LOCK

(71) Applicant: Otto Bock Healthcare Products GmbH, Vienna (AT)

(72) Inventors: Luis Sagmeister, Pitten (AT); Christoph Ledinger, Möllersdorf (AT)

(73) Assignee: Otto Bock Healthcare Products GmbH, Vienna (AT)

( * ) Notice: Subject to any disclaimer, the term of this patent is extended or adjusted under 35 U.S.C. 154(b) by 46 days.

(21) Appl. No.: 16/643,915

(22) PCT Filed: Jun. 19, 2018

(86) PCT No.: PCT/EP2018/066286
§ 371 (c)(1),
(2) Date: Mar. 3, 2020

(87) PCT Pub. No.: WO2019/048098
PCT Pub. Date: Mar. 14, 2019

(65) Prior Publication Data
US 2020/0208689 A1 Jul. 2, 2020

(30) Foreign Application Priority Data
Sep. 6, 2017 (DE) ...................... 10 2017 120 466.0

(51) Int. Cl.
*F16D 41/066* (2006.01)
*A61F 2/58* (2006.01)
(Continued)

(52) U.S. Cl.
CPC ............ *F16D 41/066* (2013.01); *A61F 2/583* (2013.01); *F16D 41/105* (2013.01);
(Continued)

(58) Field of Classification Search
CPC ...... F16D 41/066; F16D 41/064; F16D 41/06; F16D 41/0665; F16D 41/10; F16D 41/105; F16D 41/08; F16D 41/086; F16D 41/088; F16D 7/048; F16D 7/06; F16D 7/10; A61F 2/50; A61F 2/54; A61F 2/58; A61F 2/583;
(Continued)

(56) References Cited

U.S. PATENT DOCUMENTS 542,042 A * 7/1895 Charter ................. F16D 41/066
192/45.02
898,332 A * 9/1908 Davis ................... F16D 41/066
192/45.017
(Continued)

FOREIGN PATENT DOCUMENTS

DE 102006046495 A1 4/2008
DE 102011005049 A1 9/2012
GB 495281 A 11/1938

*Primary Examiner* — Huan Le
(74) *Attorney, Agent, or Firm* — Holland & Hart LLP

(57) ABSTRACT

A jamming roller lock with a housing and at least two jamming discs, which are arranged in the housing such that they can be rotated and which each comprise at least one recess, in which a jamming roller is located, at least one driving projection and at least one driven projection, wherein the jamming discs are arranged and designed in such a way that a rotation of the jamming discs can be achieved by driving the driving projections and a rotation of the jamming discs is prevented by driving the driven projections.

16 Claims, 6 Drawing Sheets

(51) Int. Cl.
  *F16D 41/10* (2006.01)
  *A61F 2/68* (2006.01)
  *A61F 2/70* (2006.01)
  *F16D 41/08* (2006.01)
(52) U.S. Cl.
  CPC . *A61F 2002/6854* (2013.01); *A61F 2002/701* (2013.01); *F16D 41/088* (2013.01)
(58) Field of Classification Search
  CPC .. A61F 2/60; A61F 2/604; A61F 2/605; A61F 2/64; A61F 2/66; A61F 2002/6854; A61F 2002/6845
  See application file for complete search history.

(56) References Cited

U.S. PATENT DOCUMENTS

| | | | | |
|---|---|---|---|---|
| 1,008,428 | A * | 11/1911 | Moseson | F16D 41/088 192/44 |
| 1,362,011 | A * | 12/1920 | Kirby | F23D 11/08 192/45.017 |
| 2,050,016 | A * | 8/1936 | Murray | F16D 41/088 192/48.92 |
| 2,515,295 | A * | 7/1950 | Davis | F16D 41/088 192/17 R |
| 2,865,479 | A * | 12/1958 | Hungerford | F16D 41/066 123/185.2 |
| 4,451,939 | A * | 6/1984 | Thompson | A61F 2/64 623/40 |
| 5,165,509 | A | 11/1992 | Kanno et al. | |
| 6,575,279 | B2 | 6/2003 | Quigley | |
| 6,757,975 | B1 * | 7/2004 | Todd | B21D 53/28 192/105 CD |
| 8,715,367 | B1 | 5/2014 | Pansiera et al. | |
| 2002/0148696 | A1 | 10/2002 | Enomoto et al. | |
| 2008/0047796 | A1 * | 2/2008 | Ogata | F16D 41/066 192/45.018 |
| 2013/0119212 | A1 | 5/2013 | Benjamin et al. | |
| 2017/0001714 | A1 * | 1/2017 | Piaton | F16H 31/001 |
| 2017/0165088 | A1 | 6/2017 | Lefeber et al. | |
| 2017/0248176 | A1 * | 8/2017 | Keating | B21D 28/06 |

* cited by examiner

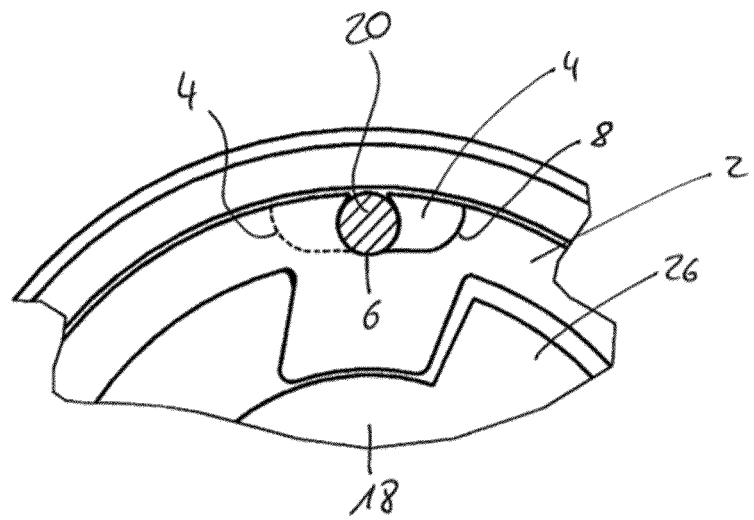
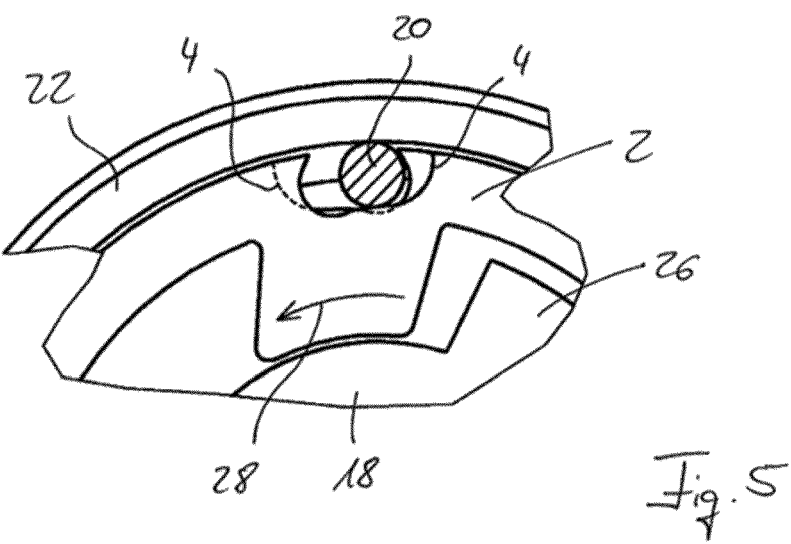
Fig. 5

JAMMING ROLLER LOCK

CROSS REFERENCE TO RELATED APPLICATIONS

This application is a U.S. National Entry and claims priority to PCT International Patent Application No. PCT/EP2018/066286, filed 19 Jun. 2018, and entitled "JAMMING ROLLER LOCK", which claims priority to Germany Patent Application No. 10 2017 120 466.0 filed 6 Sep. 2017, the entire disclosures of which are incorporated herein by this reference.

TECHNICAL FIELD

The invention relates to a jamming roller lock.

BACKGROUND

Locks and particularly jamming roller locks and other types of freewheels are used in a multitude of different applications, such as orthopedic devices, when a rotation of two components relative to one another should not be allowed in all directions or such a rotation should not be allowed to be driven from all sides. As a result, in the case of upper limb prostheses, for instance, the gripping, raising or rotating of end effectors is generally achieved by means of electric motors and corresponding gears. In most of these cases, the force—such as a grip force—once applied, should also be maintained after switching off the current from the electric motor. However, this should be achieved without the current having to be maintained in order to save energy. Generally, this function is achieved by a lock, which blocks the drive train from being activated by external forces. In some applications, this blocking occurs regardless of the external force; in other applications, blocking should only occur in one direction of rotation. In the case of upper limb prostheses, these forces may be produced, for example, by holding an object or by the wearer of the orthopedic device, i.e. generally the prosthesis, supporting themselves on the gripping device. However, it must also be ensured that the drive train can operate freely on the motor side. If it is driven by the motor, for instance the electric motor, there should be no additional resistance that obstructs the movement of the end effector. However, the connection in an arm or hand prosthesis are just two examples from a broad range of application options, in particular within the field of orthopedic devices. In this way, joints of orthoses, other components of orthoses or other prostheses can be designed with corresponding jamming roller locks.

Hand prostheses are known from the prior art which make use of a wrap spring lock in order to achieve the desired locking of the drive train against an activation caused by external forces; in the case of such a wrap spring lock, a twisting of two spring ends effects a change in diameter and thus a frictional connection of a fixed housing. This frictional connection creates the desired locking effect. This can be designed to be locking on both sides or free-running on both sides. Often simplified variations of jamming roller locks are utilised in other products and orthopedic devices, said variations generally only locking in one rotational direction and allowing a drive in the opposite direction. Here, it is often irrelevant from which side the jamming roller lock is driven, i.e. whether the acting force or the acting torque is generated by a drive device, in particular the electric motor, or by an external force or an external torque.

SUMMARY

The invention therefore aims to propose a jamming roller lock with the desired locking effects and which is simultaneously cost-effective, quick and easy to produce.

The invention solves the problem by way of a jamming roller lock with a housing and a multitude of clamping discs, which are arranged in the housing such that they can be rotated and which each comprise at least one recess, in which a jamming roller is located, at least one driving projection and at least one driven projection, wherein the clamping discs are arranged and designed in such a way that a rotation of the clamping discs can be achieved by driving the driving projections and a rotation of the clamping discs by driving the driven projections can be prevented.

The locking force can be almost arbitrarily scaled via the number of recesses and jamming rollers used.

Preferably, at least one of the jamming rollers, but preferably all jamming rollers, extends through the recess of several, but preferably all, clamping discs.

The recesses of the clamping discs are preferably open radially outwards and restricted on this side by the housing. Here, they feature a freewheel side, which is large enough to ensure that a jamming roller does not come into contact with the housing, and a locking side, which is small enough to ensure that a jamming roller comes into contact with the housing.

This operating principle of a jamming roller lock has been known within the scope of the prior art for many years. The at least one jamming roller is situated in the at least one recess, which is open radially outwards and is restricted by the housing.

If the clamping disc is now rotated, the jamming roller moves relative to the clamping disc inside the recess. In this case, if it moves on the freewheel side of the recess, it does not come into contact with the housing; rather, it can move freely on the freewheel side of the recess. This enables a rotation of the clamping disc relative to the housing. However, if the jamming roller moves on the locking side of the recess, the small size of the recess on this side means that it comes into contact with the housing and it becomes jammed between the bottom of the recess, i.e. of the jamming roller, and the housing, so that a further rotation of the clamping disc relative to the housing is not possible.

In a preferred embodiment of the jamming roller lock, the freewheel side in the clockwise direction lies in front of the locking side for one part of the clamping discs; for the other part of the clamping discs, it lies behind the locking side in the clockwise direction. Herein lies the difference between a corresponding jamming roller lock and jamming roller locks from the prior art. In general, such jamming roller locks from the prior art feature a single clamping disc or a multitude of identical clamping discs, so that the freewheel side of all clamping discs lies exclusively in front or exclusively behind the locking side, for example in the clockwise direction. As a result, a rotation of the clamping discs in the housing is only possible in one direction if, by way of the rotation, the jamming roller is moved in the freewheel side of the recess, and a rotation in the opposite direction of the clamping discs in the housing is blocked by the jamming roller, which moves as a result of the movement on the locking side of the recess and thus becomes jammed between the clamping disc and the housing. A simultaneous driving or blocking of all clamping discs is not possible with the jamming roller locks according to this embodiment.

In a preferred configuration, a driving of the driving projections in a direction of rotation only drives the clamping discs for which the freewheel side lies behind the locking side in the direction of rotation. In the case of these clamping discs, this driving causes the jamming roller to move in the freewheel side of the recess, such that a rotation is not adversely affected by these clamping discs. However, given that this is only the case for one part of of the clamping disc, only these clamping discs are driven. The other part of the clamping discs, with the freewheel side located in front of the locking side in the direction of rotation for the direction of rotation given, is not driven via the driving projections or the driven projections; rather, it is moved via the jamming roller, which functions as a driver in this case. Here, the jamming roller for this part of the locking discs is situated in the front part of the recess in the direction of rotation, wherein said front part of the recess is the freewheel side for this part of the clamping discs. This ensures that a rotation is always possible, regardless of the direction of rotation, as long as the drive occurs via the driving projections. Here, the driving projections of the first part of the clamping discs are preferably arranged at an offset to the driving projections of the other part of the locking discs, such that a corresponding driver on the driving side, which is coupled, for instance, with an electric motor or another driving device, only reaches the respective desired driving projections and can drive the corresponding clamping discs.

Preferably, the driving of the driven projections in a direction of rotation only drives the clamping discs for which the locking side lies behind the freewheel side in the direction of rotation. As a result of this drive and the corresponding movement of the locking discs, the jamming roller moves in the locking side of the recess, thereby preventing a further rotation, as the jamming roller is jammed between the bottom of the recess and the housing. This also occurs regardless of the direction of rotation given that, depending on the direction of rotation, either the one part or the other part of the locking discs is driven via the driven projections. Consequently, the driven projections of both parts of the clamping discs are also preferably arranged at an offset to one another.

It has been proven to be practical for the jamming roller lock to comprise an uneven number of clamping discs and/or at least three recesses per clamping disc. Preferably, at least one jamming roller is located in each one of these at least three recesses. The more recesses and jamming rollers provided, the greater the locking force that can be achieved. In a configuration of the jamming roller lock that is structurally particularly simple, the individual clamping discs are designed to be identical and are arranged only at an offset and, where applicable, twisted in relation to one another. This renders it possible to reduce the number of different components required for the construction of the jamming roller lock.

In a preferred configuration, the clamping discs are made of a metallic material. Alternatively or additionally, plastics, wood or wooden materials, or other materials may be used. For example, they may be extruded, punched, laser cut, water jet cut, sawn or injection moulded.

The invention also solves the problem by way of an orthopedic device with a driving device, which is coupled with at least one driver on the driving side, and an end effector, which is coupled with a driver on the driven side, and a jamming roller lock of the type described here, wherein the driver on the driving side is or can be engaged with the driving projections and the driver on the driven side is or can be engaged with the driven projections.

If the end effector is driven via the driving device, a rotation of the driver on the driving side is first of all effected via the driving device. Said driver is coupled with the driving projections, so that preferably only those clamping discs are driven for which the freewheel side lies behind the locking side in the direction of rotation. As a result, a rotation of the clamping discs in the housing can be achieved without any additional resistance. This also effects a driving of the driver on the driven side as well as a transfer of the torque exerted by the driving device to the end effector.

However, if an external torque or force is applied to the end effector, this torque or force is transferred to the driver on the driven side, which is or can be engaged with the driven projections. However, when driving these driven projections, it is preferable if only the part of clamping discs is driven for which the locking side lies behind the freewheel side in the direction of rotation. As explained above, this leads to a locking of the jamming roller lock.

BRIEF DESCRIPTION OF THE DRAWINGS

In the following, an example of an embodiment of the present invention will be explained in more detail by way of the attached figures: They show FIG. 1—a clamping disc for a jamming roller lock according to a first example of an embodiment of the invention, FIG. 2—a part of an orthopedic device in an exploded view, FIG. 3—the top view of a driven side of the device from FIG. 2, FIG. 4—the top view of a driving side of the device from FIG. 2, FIG. 5—two detailed views of a jamming roller lock and FIG. 6—an orthopedic device according to a further example of an embodiment of the present invention in an exploded view.

DETAILED DESCRIPTION

Figure 1:
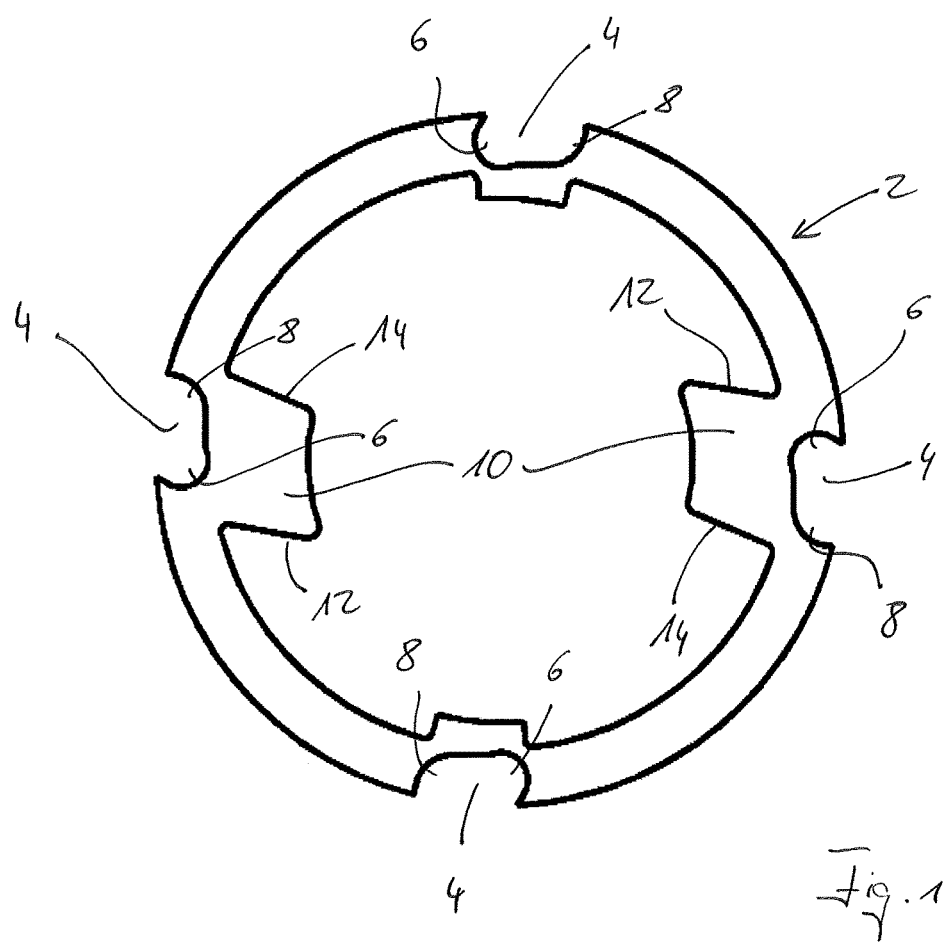

FIG. 1 depicts a clamping disc 2 for a jamming roller lock according to a first example of an embodiment of the invention. The clamping disc 2 has four recesses 4, which are evenly distributed across the circumference in the example of an embodiment shown. Each recess has a freewheel side 6 and a locking side 8. The recesses 4 are open on the radially outward side and, when a jamming roller lock is mounted, restricted by a housing.

Two projections 10 project radially inwards: for each projection, one side forms a driving projection 12 and the opposite side a driven projection 14. Of course, a driving projection 12 and a driven projection 14 may also be separate projections.

Figure 2:
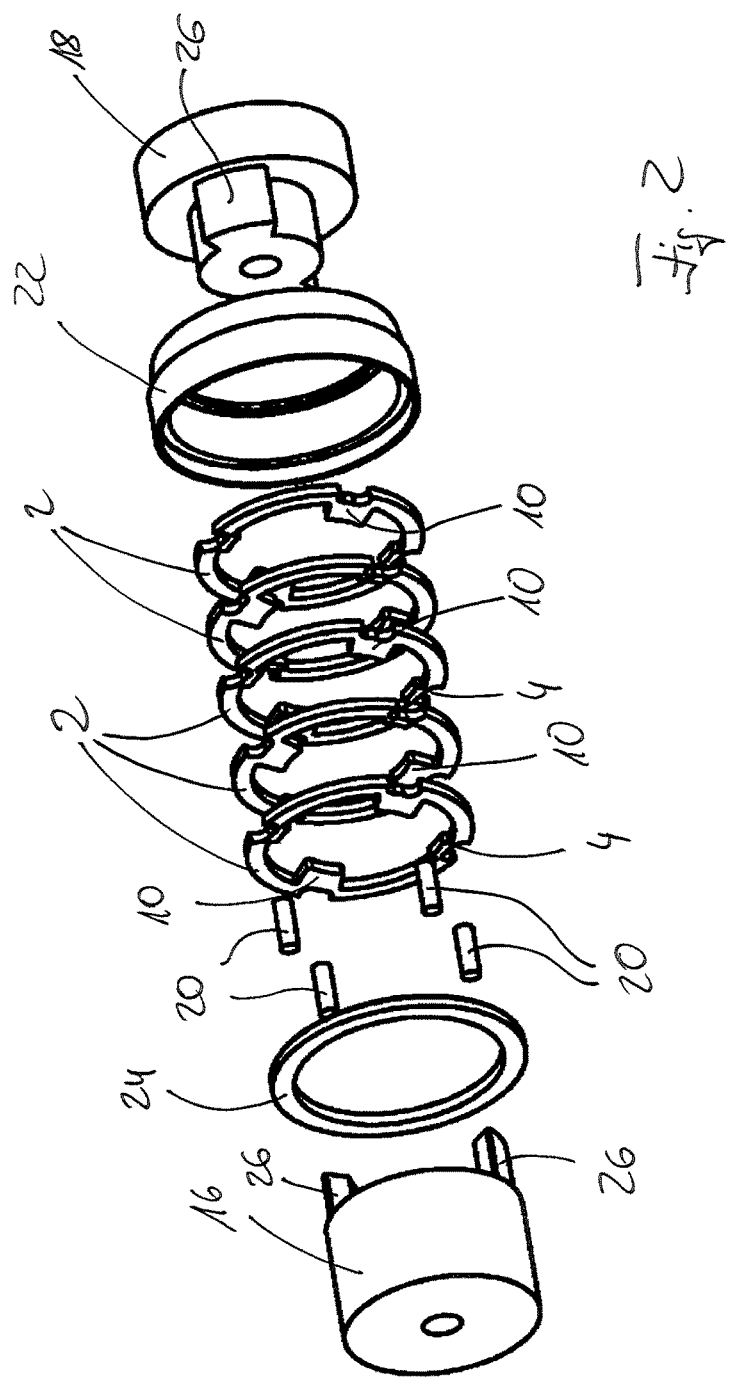

FIG. 2 depicts an exploded view of a jamming roller lock according to an example of an embodiment of the present invention with a driver on the driving side 16 and a driver on the driven side 18. The jamming roller lock features five clamping discs 2, each of which has four recesses 4, as depicted in FIG. 1. Inside said recesses are four jamming rollers 20. The clamping discs 2 with the jamming rollers 20 are situated in a housing 22, which restricts the recesses 4 radially outwards. In the example of an embodiment shown, a cover disc 24 prevents the jamming rollers 20 from being able to slip out of the recesses 4 in the axial direction.

Both the driver on the driving side 16 and the driver on the driven side 18 feature driver claws 26, with which they are or can be engaged with the driving projections 12 or the driven projections 14.

In FIG. 2, it is clear that the clamping discs 2 are arranged at an offset to one another, such that an angle between the projections 10 of two adjacent clamping discs 2 in the example of an embodiment shown is 90°.

Figure 3:
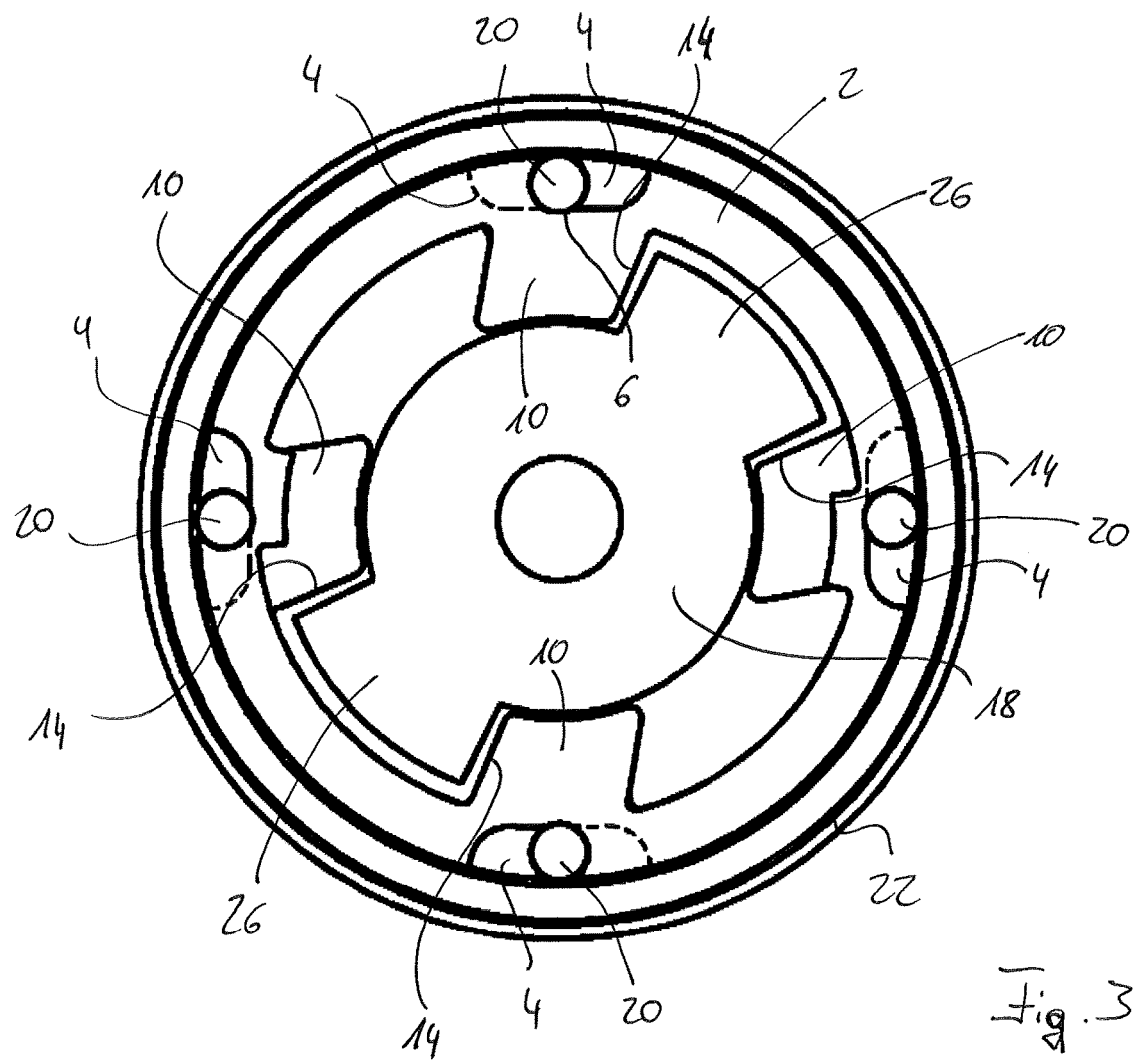

FIG. 3 shows a top view on a driven side of such a device. The driver on the driven side 18 with the two driver claws 26 are visible, as well as a clamping disc 2 with two projections 10. The two driver claws 26 of the driver on the driven side 18 can be engaged with the respective driven projection 14 of the projection 10 by effecting a rotation of the driver on the driven side 18.

FIG. 3 also depicts two further projections 10, which are on the right-hand side and the left-hand side in FIG. 3. These belong to a clamping disc 2 which is arranged behind the depicted clamping disc 2. These projections 10 also feature driven projections 14, which can be engaged with driver on the driven side 18 via the driver claws 26.

The front clamping disc 2 comprises the four recesses 4 in each of which a jamming roller 20 is arranged, each of which is situated on the freewheel side 6 in the example of an embodiment shown. The recesses 4 of the other locking disc 2 behind the locking disc 2 are indicated with a dashed line. The respective jamming roller 20 of these recesses 4 is also on the freewheel side 6.

If, in the example of an embodiment shown, the driver on the driven side 18 is now caused to rotate, the driver claws 26 engage either with the driven projections 14 of the front clamping disc 2 or the driven projections 14 of the clamping disc 2 behind it. If, for example, the driver on the driven side 18 is rotated anti-clockwise, its driver claws 26 engage with the driven projections 14 of the front clamping disc 2. Consequently, these are also rotated anti-clockwise, causing the jamming rollers 20 in the respective recesses 4 to be moved to the respective locking side 8. This results in a locking of the jamming roller lock, as the jamming rollers 20 become jammed between the base or the bottom of the recess 4 and the housing 22.

Conversely, if the driver on the driven side 18 is rotated clockwise, its driver claws 26 engage with the driven projections 14 of the rear clamping disc 2. These are then also moved in the clockwise direction, again causing the jamming rollers 20 in the recesses 4 of this clamping disc 2 to be moved from the freewheel side 6 to the locking side 8, so that a locking also occurs in this case. Regardless of the direction in which the driver on the driven side 18 is consequently moved, a locking of the jamming roller lock always occurs.

Figure 4:
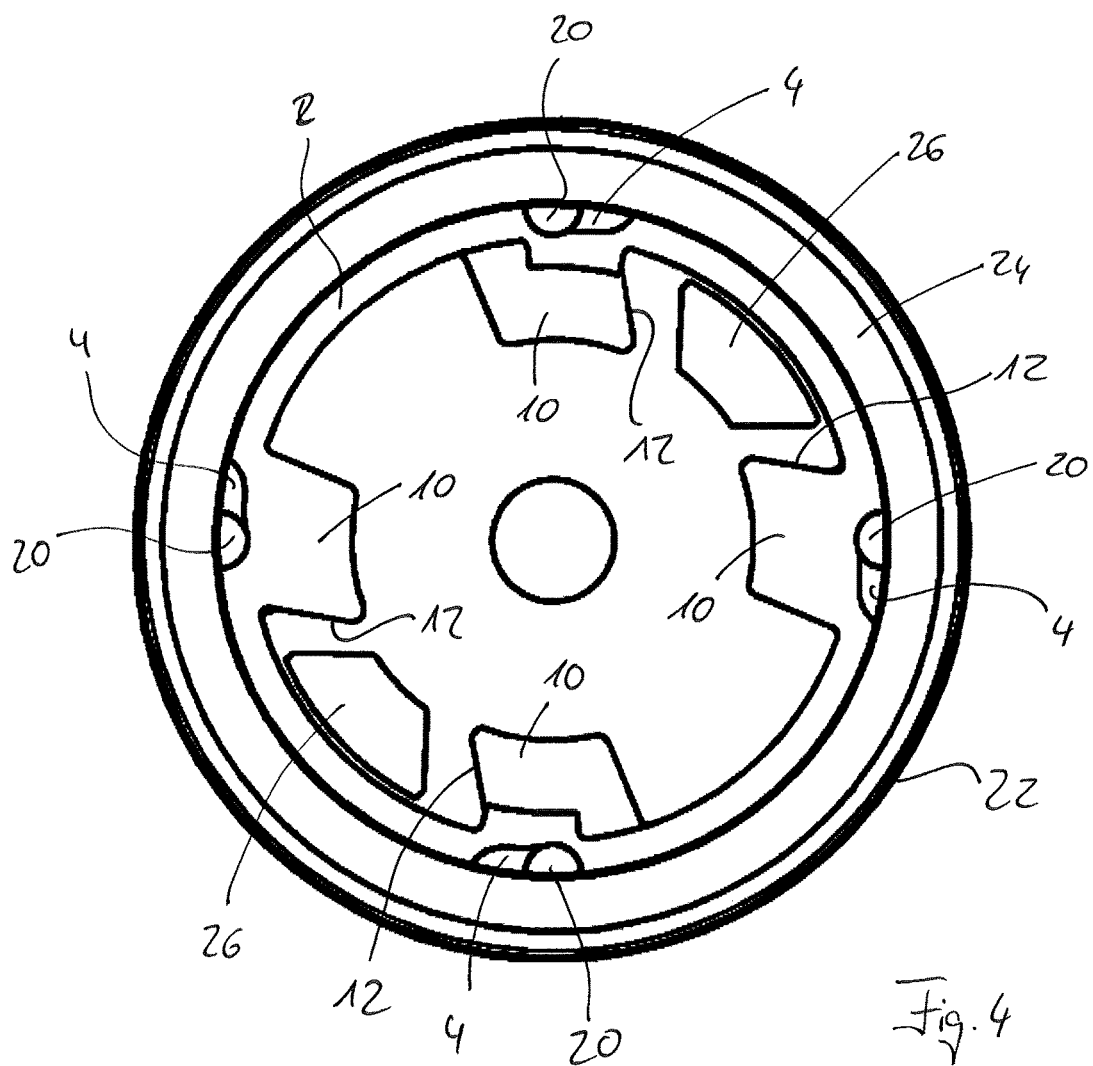

FIG. 4 shows a top view on a driven side of such a jamming roller lock. The recesses 4 can be seen, in each of which a jamming roller 20 is situated; however, in the example of an embodiment shown, these are partially covered by the cover disc 24. Each jamming roller 20 is situated on the freewheel side 6 of the recess 4. The two driver claws 26 of the driver on the driving side 16 are also depicted. The two projections 10 on the right and the left belong to the clamping disc 2 that is at the front in this direction, whereas the upper and lower projections 10 belong to the clamping disc behind. Each of the projections 10 has a driving projection 12, which can engage with the respective driver claw 26.

If the driver on the driving side 16 is moved, with its driver claws 26, in the clockwise direction, the driver claws 26 engage with the driving projections 12 of the projections 10 depicted to the right and the left in FIG. 4. This front clamping disc 2, to which these projections 10 belong, is also moved clockwise, so that the jamming rollers 20 remain on the freewheel sides 6 of the recesses 4. A rotation is therefore possible.

However, if the driver on the driving side 16 is moved, with its driver claws 26, in the anti-clockwise direction, the driver claws 26 engage with the driving projections 12 of the upper and lower projections 2 in FIG. 4, which belong to the clamping disc behind the depicted clamping disc 2. As shown in FIG. 4, in the case of this clamping disc 2, the locking side 8 of the recess 4 for this anti-clockwise direction of rotation is situated in front of the corresponding freewheel side 6, so that a rotation of the clamping disc 2 relative to the housing 22 is also possible in this direction of rotation.

Regardless of in which direction the driver on the driving side 16 is rotated, a rotation is thus always possible.

This is clear in FIG. 5. The upper section of FIG. 5 shows a jamming roller 20 situated in a recess 4 of the front clamping disc 2, wherein the recess 4 is depicted by a solid line. For this recess 4, the locking side 8 is on the right-hand side of the recess 4 and the freewheel side 6, in which the jamming roller 20 is situated, is on the left. The recess 4 of the rear clamping disc 2 is also depicted by a dashed line, said recess now being positioned the other way round. The freewheel side 6 is on the right, whereas the locking side 8 is on the left. A driver claw 26 of the driver on the driven side 18 can also be seen.

The lower section of FIG. 5 shows what happens if the front clamping disc 2 is caused by the driver on the driven side 18 to rotate along the arrow 28, i.e. anti-clockwise in the example of an embodiment shown. The two recesses 4, again depicted by the solid line in the case of the front clamping disc 2 and the dashed line for the clamping disc behind it, are displaced relative to one another and in the recess 4 of the front clamping disc 2, the jamming roller 20 is moved to the right, i.e. towards the locking side 8. As a result, it becomes jammed between the clamping disc 2 and the housing 22 and a further rotation of the clamping disc relative to the housing 22 is prevented.

Figure 6:
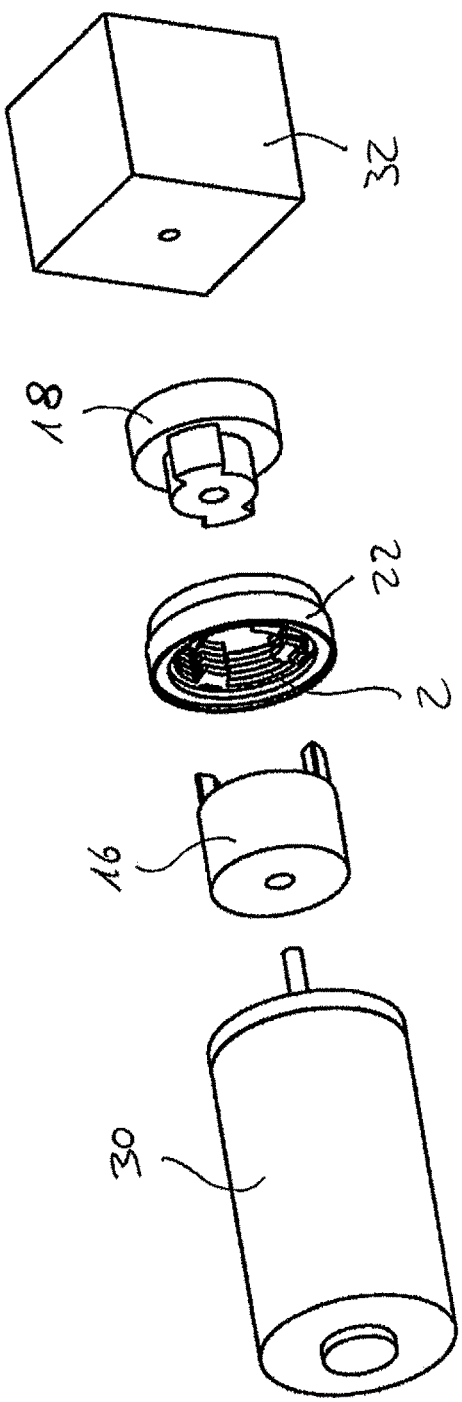

FIG. 6 depicts a schematic exploded view of a part of an orthopedic device with a driving device 30, a driver on the driving side 16, the jamming roller lock with the housing 22 and the clamping discs 2 arranged within it, and a driver on the driven side 18, which is coupled with an end effector 32, depicted only schematically.

We claim:

1. A jamming roller lock, comprising:
   a housing;
   at least two clamping discs which are arranged in the housing such that they can be rotated, the clamping discs comprising:
   at least one recess in which a jamming roller is positioned;
   at least one driving projection; and
   at least one driven projection;
   wherein the clamping discs are arranged and designed in such a way that rotation of the clamping discs is possible by driving the driving projections, and a rotation of the clamping discs by driving the driven projections is prevented;
   wherein the recesses of the clamping discs are open radially outwards and are restricted by the housing on a radial outward side of the clamping discs, and the at least two clamping discs each define a freewheel side of the recess extending from the clamping disc which is large enough to ensure that a clamping roller does not come into contact with the housing, and a locking side of the recess extending from the clamping disc which is small enough to ensure that the jamming roller comes into contact with the housing; and wherein one part of the freewheel side of the recess extends beyond the locking side in a clockwise direction, and another part of the freewheel side of the recess lies behind the locking side in the clockwise direction.

2. The jamming roller lock according to claim 1, wherein the jamming roller extends through the at least one recess of at least one of the at least two clamping discs.

3. The jamming roller lock according to claim 1, wherein, by driving the driving projections in one direction of rotation, only those clamping discs are driven for which the freewheel side lies behind the locking side in the direction of rotation.

4. The jamming roller lock according to claim 1, wherein, by driving the driven projections in one direction of rotation, only those clamping discs are driven for which the locking side lies behind the freewheel side in the direction of rotation.

5. The jamming roller lock according to claim 1, wherein the jamming roller lock comprises at least three and an odd number of clamping discs and at least three recesses per clamping disc.

6. The jamming roller lock according to claim 1, wherein the clamping discs have the same contour.

7. The jamming roller lock according to claim 1, wherein the clamping discs comprise at least one of a metallic material and a ceramic material.

8. An orthopedic device, comprising:
a driving device, which is coupled with at least one driver on a driving side;
an end effector, which is coupled with a driver on a driven side;
a jamming roller lock, comprising:
a housing;
at least two clamping discs which are arranged in the housing such that they can be rotated, the clamping discs comprising:
at least one recess in which a jamming roller is positioned;
at least one driving projection; and
at least one driven projection;
wherein the clamping discs are arranged and designed in such a way that rotation of the clamping discs is possible by driving the driving projections, and a rotation of the clamping discs by driving the driven projections is prevented; and
wherein the driver on the driving side is or can be engaged with the driving projections and the driver on the driven side is or can be engaged with the driven projections.

9. A jamming roller lock, comprising:
a housing;
at least one jamming roller;
at least two clamping discs rotatably arranged in the housing and each comprising:
at least one recess in which the at least one jamming roller is positioned;
at least one driving projection;
at least one driven projection;
wherein driving the driving projections rotates the clamping discs, and fixing a position of the driven projections prevents rotation of the clamping discs;
wherein the recesses of the clamping discs are open radially outwards and are restricted by the housing on a radial outward side of the clamping discs, and the at least two clamping discs each define a freewheel side of the recess extending from the clamping disc which is large enough to ensure that a clamping roller does not come into contact with the housing, and a locking side of the recess extending from the clamping disc which is small enough to ensure that the jamming roller comes into contact with the housing; and
wherein one part of the freewheel side of the recess extends beyond the locking side in a clockwise direction, and another part of the freewheel side of the recess lies behind the locking side in the clockwise direction.

10. The jamming roller lock according to claim 9, wherein the at least one jamming roller extends through the at least one recess of at least one of the at least two clamping discs.

11. The jamming roller lock according to claim 9, wherein, by driving the driving projections in one direction of rotation, only those clamping discs are driven for which the freewheel side lies behind the locking side in the direction of rotation.

12. The jamming roller lock according to claim 9, wherein, by driving the driven projections in one direction of rotation, only those clamping discs are driven for which the locking side lies behind the freewheel side in the direction of rotation.

13. The jamming roller lock according to claim 9, wherein the jamming roller lock comprises at least three and an odd number of clamping discs and at least three recesses per clamping disc.

14. The jamming roller lock according to claim 9, wherein the clamping discs have a matching contour.

15. The jamming roller lock according to claim 9, wherein the clamping discs comprise at least one of a metallic material and a ceramic material.

16. An orthopedic device, comprising:
a driving device coupled with at least one driver on a driving side;
an end effector coupled with a driver on a driven side;
a jamming roller lock, comprising:
a housing;
at least two clamping discs which are arranged in the housing such that they can be rotated, the clamping discs comprising:
at least one recess in which a jamming roller is positioned;
at least one driving projection; and
at least one driven projection;
wherein the clamping discs are arranged and designed in such a way that rotation of the clamping discs is possible by driving the driving projections, and a rotation of the clamping discs by driving the driven projections is prevented; and
wherein the driver on the driving side is engaged with the driving projections and the driver on the driven side is engaged with the driven projections.

* * * * *